(12) United States Patent
Tay et al.

(10) Patent No.: US 9,206,102 B2
(45) Date of Patent: Dec. 8, 2015

(54) PREPARATION OF AN ETHER COMPOUND

(71) Applicants: RHODIA OPERATIONS, Paris (FR); CENTRE NATIONAL DE LA RECHERCHE SCIENTIFIQUE (C.N.R.S.), Paris (FR)

(72) Inventors: Astrid Tay, Shanghai (CN); Floryan Decampo, Shanghai (CN); Xiaoshuang Feng, Shanghai (CN); Wenjuan Zhou, Shanghai (CN); Jean Marc Clacens, Shanghai (CN)

(73) Assignees: Rhodia Operations, Paris (FR); Centre National De La Recherche Scientifique, Paris (FR)

( * ) Notice: Subject to any disclaimer, the term of this patent is extended or adjusted under 35 U.S.C. 154(b) by 0 days.

(21) Appl. No.: 14/400,036

(22) PCT Filed: May 10, 2013

(86) PCT No.: PCT/CN2013/075443
§ 371 (c)(1),
(2) Date: Nov. 10, 2014

(87) PCT Pub. No.: WO2013/166985
PCT Pub. Date: Nov. 14, 2013

(65) Prior Publication Data
US 2015/0112099 A1    Apr. 23, 2015

(30) Foreign Application Priority Data
May 11, 2012   (WO) ................ PCT/CN2012/075379
Jul. 3, 2012    (WO) ................ PCT/CN2012/078114

(51) Int. Cl.
*C07C 41/09* (2006.01)
*C07C 41/34* (2006.01)

(52) U.S. Cl.
CPC ................ *C07C 41/09* (2013.01); *C07C 41/34* (2013.01)

(58) Field of Classification Search
None
See application file for complete search history.

(56) References Cited

U.S. PATENT DOCUMENTS

2007/0238905 A1* 10/2007 Arredondo ............. C07C 41/09 568/672
2008/0306211 A1* 12/2008 Lemke .................. C07C 41/09 525/50

* cited by examiner

*Primary Examiner* — Rosalynd Keys

(57) ABSTRACT

A process for the preparation of an ether compound is disclose, wherein the ether compound is prepared via a reaction from at least an alcohol (I) and an alcohol (II), optionally using a catalyst X, wherein alcohol (I) and alcohol (II) are forming a biphasic liquid system when mixed together; comprising at least the following steps: a) Producing an alcohol (I)/alcohol (II) emulsion by using as stabilizing species amphiphilic solid particles of nanometric dimension; optionally comprising a catalyst X; b) Proceeding to the reaction of the ether compound by setting temperature, and c) Isolating the ether compound.

20 Claims, No Drawings

PREPARATION OF AN ETHER COMPOUND

This application is a U.S. national phase entry under 35 U.S.C. §371 of International Application No. PCT/CN2013/075443, filed on May 10, 2013, which claims priority to International Application Nos. PCT/CN2012/075379, filed on May 11, 2012, and PCT/CN2012/078114, filed on Jul. 3, 2012. The entire contents of these applications are explicitly incorporated herein by reference for all purposes.

The present invention concerns a process for the preparation of an ether compound via a reaction from at least an alcohol (I) and an alcohol (II), optionally using a catalyst X, wherein alcohol (I) and alcohol (II) are forming a biphasic liquid system when mixed together; comprising at least the following steps: a) Producing an alcohol (I)/alcohol (II) emulsion by using as stabilizing species amphiphilic solid particles of nanometric dimension; optionally comprising a catalyst X; b) Proceeding to the reaction of the ether compound by setting temperature, and c) Isolating the ether compound.

PRIOR ART

Very often chemical reactions involve reactants that are not miscible such as with two incompatible phases, a hydrophobic phase and a hydrophilic phase. To solve this miscibility issue, a co-solvent can be used. However, after the synthesis this solvent must be removed.

A way to help the reactant meet without any solvent, is to emulsify the two reactants in order to create more reacting interface. However strong stirring and heating sometimes do not create enough reactive interface. A way to help stabilize the emulsion is to use an emulsifier, but even if the quantity involved is quite low compared to the reactants the separation issue is still present after the synthesis and there is then a need of a further chemical step.

In the special case of surfactant synthesis the product itself can be used as emulsifier. However the quantity needed to homogenize the mixture is not negligible and acts against the yield and the productivity.

If emulsions are not very privileged, there are several examples, including industrial processes, where syntheses are performed in these particular conditions such as with emulsion polymerization to prepare polymers. In 1950 Homer and Truter published in Nature (Nature 165, 771) that wool wax hydrolysis kinetics is improved when the reaction is performed in an emulsion. Jacobson et al. report Enhanced Catalyst Reactivity and Separations Using Water/Carbon Dioxide Emulsions stabilized by surfactants in 1999 (J. Am. Chem. Soc. 1999, 121, 11902-11903)

Emulsion stabilized by particles are reported since early 20th century, it is also known as Pickering emulsion known since Pickering, S. U. 1907, J. Chem. Soc. 91 Pages 2001-2021. Aveyard et al. published good a review in Advances in Colloid and Interface Science 100-102 (2003) 503-546. Most of academic on pickering emulsions are conducted on water/oil systems.

Binks et al. (Phys. Chem. Chem. Phys., 2000, 2, 2959-2967) studied the effect of non aqueous phase type solvent on toluene/solvent Pickering emulsions. It is one of the rare paper mentioning non aqueous polar system. Authors have prepared emulsions of toluene with different other liquids including formamide, glycerol and ethylene glycol, however emulsion could not be obtained with the last two liquids, in particular glycerol.

Yang et al. (Applied Catalysis A: General 382 (2010) 131-137) demonstrate that in presence of water, it is possible to do selective aerobic oxidation of alcohol with solid catalyst at the alcohol/water interface. Resasco et al. (Science Vol 327 2010 and Adv. Synth. Catal. 2010, 352, 2359-2364) mention about "Solid Nanoparticles that Catalyze Reactions at the specific Water/Oil Interface". The reaction of their focus is a phase transfer reaction where the reactants are in the water droplet and the product of the reaction is transferred to the oil phase allowing thus to increase the conversion.

All of these references concern use of particles to stabilize emulsion of two solvents always using water. There was a need then to develop a new process permitting to carrying out a reaction synthesis involving a medium with a hydrophobic phase and a hydrophilic phase, without the presence of co-solvent or surfactants.

INVENTION

It appears that it is now possible to produce a compound via a reaction involving two immiscible alcohols that are usually forming a biphasic liquid system when mixed together; by using amphiphilic solid particles of nanometric dimension, notably comprising at the surface both hydrophilic and hydrophobic functions. Such a synthesis reaction may be made without the presence of co-solvent or surfactant.

The present invention then concerns a process to produce at least an ether compound via a reaction from at least an alcohol (I) and an alcohol (II), optionally using a catalyst X, wherein alcohol (I) and alcohol (II) are forming a biphasic liquid system when mixed together; comprising at least the following steps:

a) Producing an alcohol (I)/alcohol (II) emulsion by using as stabilizing species amphiphilic solid particles of nanometric dimension; optionally comprising a catalyst X;
b) Proceeding to the reaction of the ether compound by setting temperature, and
c) Isolating the ether compound.

Such amphiphilic solid particles of nanometric dimension can be removed easily after the synthesis, notably by centrifugation, by flocculation of filtration without engaging complex separation of co-solvent or surfactants. Said solid particles can be easily separated furthermore from the liquid system and reused.

Process of the present invention notably permits to carry out the reaction increasing the reaction yield and/or the reaction selectivity, notably by controlling some parameters, such as the size of the droplets for example.

In a general way, phase separation occurs because the interfacial tension between the two liquids is high. One way to reduce this interfacial tension is to modify this interface by adsorbing an object. Most commonly used objects are surfactants molecules.

Emulsion stabilized by particles relies on the fact that once a particle is adsorbed at the interface it is often difficult to remove it. The necessary energy EE to remove an adsorbed particle is given by the following expression:

$$\Delta E = \pi r^2 \gamma_{he}(1 \pm \cos \theta_{he})^2$$

wherein: r is the particle radius, $\gamma_{he}$ is the interfacial tension between the two liquids and $\theta_{he}$ is the contact angle of the particle in one of the phase.

From this expression, it can be seen that the adsorption energy highly depends on the particle radius and its wettability.

A "hydrophilic" molecule or portion of a molecule is one that has a tendency to interact with or be dissolved by water and other polar substances.

A "hydrophobic" molecule or portion of a molecule is one that is repelled from a mass of water and other polar substances.

"Amphiphilic" is a term describing a chemical compound possessing both hydrophilic and hydrophobic properties. Such a compound is called amphiphilic or amphipathic.

An "emulsion" is a suspension made of a first liquid in a phase made of a second liquid with which the first liquid is not miscible with the second liquid. A discontinuous phase within a continuous phase is then obtained.

Alkyl as used herein means a straight chain or branched saturated aliphatic hydrocarbon. Aryl as used herein means a 6-carbon monocyclic or 10-carbon bicyclic aromatic ring system wherein 0, 1, 2, 3, or 4 atoms of each ring are substituted by a substituent. Examples of aryl groups include phenyl, naphthyl and the like. The term "arylalkyl" or the term "aralkyl" refers to alkyl substituted with an aryl. The term "arylalkoxy" refers to an alkoxy substituted with aryl. Alkenyl as used herein means a straight chain or branched, non-cyclic or cyclic, unsaturated aliphatic hydrocarbon. Alkoxy as used herein is O-alkyl, wherein alkyl is as defined above.

As previously defined, alcohol (I) and alcohol (II) are forming a biphasic liquid system when mixed together. A person skilled in the art is then perfectly able to define the couple of alcohol (I) and alcohol (II) used in the present invention.

It is perfectly possible to evaluate the immiscibility of alcohol (I) and alcohol (II) according to the following protocol P: 50% vol of alcohol (I) and 50% vol of alcohol (II) are blended together and set a temperature T of 5° C. above the highest melting point of alcohol (I) or alcohol (II), and under atmospheric pressure. The blend is stirred for 5 mins and 30 mins settling. As example of temperature T to be used in the present protocol P, when glycerol (melting point of 18° C.) and dodecanol (melting point of 24° C.) are used, then the test temperature T is 29° C.

Alcohols (I) or (II) may be any kinds of aliphatic or aryl alcohol providing at least one hydroxyl function. These alcohols may be primary or secondary alcohols.

Alcohol (I) may notably be a hydrophilic alcohol.

A hydrophilic alcohol (I) according to the present invention is preferably an alcohol with a value P<1 according to the following expression:

$P=[\text{alcohol}(I)]\text{octanol}/[\text{alcohol}(I)]\text{unionized water}$

A stock solution of the compound is prepared in either water pre-saturated with n-octanol or n-octanol pre-saturated with water. The concentration of this stock solution is known precisely before it is employed in the determination of the partition coefficient. In a separation flask, to a given volume of this solution is added the exact same volume of the other solvent (respectively n-octanol pre-satured with water or water pre-saturated with n-octanol). After addition, the flask is hand shaken for 30 seconds. After separation of the two phases, the compound concentration is determined in each phase. This may be done by taking an aliquot of each of the two phases and analyzing them by the chosen procedure. The total quantity of substance present in both phases should be calculated and compared with the quantity of the substance originally introduced. The partition coefficient P is then calculated following the above equation.

Hydrophilic alcohol (I) of the present invention may notably be a compound of formula (I) as follows:

$$R^1(OH)p \quad \quad (I)$$

wherein $R^1$ represents the skeleton moiety of the alcohol, p is an integer ranging from 1 to 20.

$R^1$ may represent an alkyl, aryl, alkenyl or alkoxy radical, notably comprising 1 to 3000 carbon atoms. Radical $R^1$ may comprise one or several heteroatom(s) such as O or N. More, preferably $R^1$ represents the skeleton moiety of a glycerol with p is 3.

In a first embodiment, hydrophilic alcohol (I) may notably be a (poly)glycerol, defined as an oligomeric and/or polymeric chain composed of monomeric glycerol (i.e., HOCH$_2$CH(OH)CH$_2$OH) bonded together by ether linkages at the hydroxyl residue.

Specific examples of the alcohol (I) preferably having 2 to 6 hydroxyl groups may include ethylene glycol, diethylene glycol, polyethylene glycol, propylene glycol, dipropylene glycol, polypropylene glycol, 1,4-butylene glycol, 1,6-hexylene glycol, 1,8-octylene glycol, 1,10-decylene glycol, neopentyl glycol, trimethylol ethane, trimethylol propane, glycerol, diglycerol, pentaerythritol and sorbitol. These polyols may be used alone or in the form of a mixture of any optional two or more thereof. Among these polyols, from the viewpoint of a good applicability of the resultant polyglyceryl ether derivatives, preferred are glycerol, polyglycerol or mixtures thereof. The most preferred polyglycerols useful in the present invention have 2 to 30, preferably 2-20, more preferably 2-10, and most preferably 3-4 glycerol units.

In an other embodiment, alcohol (I) according to the present invention may notably be a polysaccharide, notably having the general formula $C_x(H_2O)_y$, where x is usually a number between 200 and 2500.

Alcohol (II) may notably be a hydrophobic alcohol.

A hydrophobic alcohol (II) according to the present invention is preferably an alcohol with a value P>1 according to the following expression as previously defined.

Hydrophobic alcohol may be a hydrophobic fatty alcohols that can be defined with the formula (II) as follows:

$$R^2(OH) \quad \quad (II)$$

wherein $R^2$ represents an alkyl, aryl, alkenyl or alkoxy radical comprising 6 to 36 carbon atoms. Radical $R^2$ may comprise one or several heteroatom(s) such as O or N.

Specific examples of the monoalcohol include 2-ethylhexyl alcohol, octyl alcohol, decyl alcohol, lauryl alcohol (dodecanol), myristyl alcohol, palmityl alcohol, stearyl alcohol, isostearyl alcohol, oleyl alcohol, ethylene glycol monomethyl ether, ethylene glycol monoethyl ether, ethylene glycol monopropyl ether, ethylene glycol monobutyl ether, propylene glycol monomethyl ether, propylene glycol monoethyl ether, propylene glycol monopropyl ether, propylene glycol monobutyl ether, polyethylene glycol monomethyl ether, polyethylene glycol monoethyl ether, polyethylene glycol monopropyl ether, polyethylene glycol monobutyl ether, polypropylene glycol monomethyl ether, polypropylene glycol monoethyl ether, polypropylene glycol monopropyl ether and polypropylene glycol monobutyl ether.

These fatty alcohols may be used alone or in the form of a mixture of any optional two or more thereof. Among these fatty alcohols, from the viewpoint of a good applicability of the resultant polyglyceryl ether derivatives, especially preferred are lauryl alcohol, 2-ethylhexyl alcohol and isostearyl alcohol.

In a general way, the molar ratio of alcohol (I) to alcohol (II) is preferably from 0.01 to 50, more preferably from 0.5 to 4. More specifically, the molar ratio of hydrophilic alcohol (I) to hydrophobic alcohol (II) is preferably from 0.01 to 50, more preferably from 0.5 to 4.

Ether compounds according to the present invention are a class of organic compounds that contain at least an ether group, meaning an oxygen atom connected to two alkyl or aryl groups. A lot of ether compounds may be produced by deshydratation of alcohol (I) and alcohol (II) according to the present invention.

An example illustrating the present invention is a direct route to produce, via trans-etherification, a mono alkyl glyceryl ether, called as MAGE, from a mono-alcohol and a poly-alcohol, using an appropriate catalyst.

According to this route, said mono alkyl glyceryl ether may be a compound of formula (III) as follows:

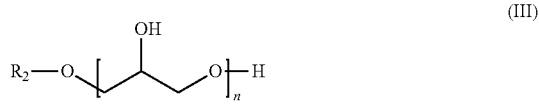

(III)

wherein $R^2$ is previously defined and n is comprised between 1 and 20.

Any catalysts able to afford synthesis of ether compounds from alcohol (I) and alcohol (II) by a deshydratation reaction may be used in the process of the present invention. Examples of catalysts used in the present invention are acid or base catalysts, homogeneous or heterogeneous catalysts; such as for example Brønsted acids, sulfonic acids, phosphoric acids and carboxylic acids.

Sulfonic acid catalysts are preferably chosen in the group consisting of: triflate acid (TFA), p-toluenesolufonic acid (PTSA), dodecyl benzyl sulfonic acid (DBSA), 10-camphorsulfonic acid (CSA), alkoxyglyceryl sulfonic acids (AGSA).

Basic catalysts are preferably chosen in the group consisting of: organic amino catalyst such as guanidine or pyridine for example, or inorganic base catalyst.

The amount of catalyst X used in the present reaction is usually comprised between 0.01 and 100% molar, preferably between 5 and 10% molar, per mol of alcohol (I) or alcohol (II). More preferably, the amount of catalyst X used in the present reaction is usually comprised between 0.01 and 100% molar, preferably between 5 and 10% molar, per mol of hydrophobic fatty alcohol.

Solid particles of nanometric dimension of the instant invention are notably isotrope or anisotrope particles, having generally a medium diameter comprised between 2 and 200 nm, preferably between 10 and 50 nm. This can be determined by visually examining a micrograph of a transmission electron microscopy "TEM" image, measuring the diameter of the particles in the image, and calculating the average primary particle size of the measured particles based on magnification of the TEM image. One of ordinary skill in the art will understand how to prepare such a TEM image and determine the primary particle size based on the magnification. The primary particle size of a particle refers to the smallest diameter sphere that will completely enclose the particle. As used herein, the term "primary particle size" refers to the size of an individual particle as opposed to an agglomeration of two or more individual particles.

The shape or morphology of the solid particle stabilizer can vary. For example, generally spherical morphologies can be used, as well as particles that are cubic, platy, or acicular (elongated or fibrous), such as sticks or needles.

Any solid particles that act as a stabilizer may be used in the present invention. Suitable particles include, for example, inorganic materials, such as water insoluble metal salts or metal hydroxides or metal oxides or mixed metal oxides or clays. Specific non-limiting examples include bentonite, tin oxide, magnesium aluminum silicate, magnesium oxide, titanium oxide, barium sulphate and/or silica, such as is described in U.S. Pat. No. 4,833,060 at col. 4, lines 54-61, the cited portion of which being incorporated herein by reference, and alumina as described in United States Patent Application Publication 2005/0156340.

Said particles are usually inorganics such as for example made of an oxide, hydroxide and/or oxy-hydroxyde of at least one metal chosen from cerium, aluminium, titanium or silicium. Particles of the invention may also be made of a phosphate or a hydrogenophosphate of metals or rare earths.

Particles can also be organic, obtained from reticulation of polymer chains such as latex particles, polymeric nanoparticles with core-shell structures which are composed by amphiphilic chains cross-linked at the core or on the layer of shell.

It can be advantageous that the particles of the invention may have a colloidal behaviour, preferably with an inter particular agglomeration rate (number of agglomerated particles/total number of particles) inferior or equal to 5%, more preferably inferior or equal to 2%. In certain embodiments, the solid particles, such as silica and/or alumina particles, are introduced in the form of colloidal dispersion, wherein finely divided solid particles are dispersed within a continuous medium in a manner that prevents them from being filtered easily or settled rapidly.

Particles of the invention are amphiphilic and then comprise at their surface both hydrophilic and hydrophobic functions.

Hydrophilic nature is usually provided by the presence of hydrophilic groups. These groups may be neutral (—OH, —COOH, —PO$_3$H$_2$, —SO$_3$H as example) or preferentially under their anionic or cationic corresponding forms.

According to an embodiment of the present invention, amphiphilic solid particles of nanometric dimension may provide a catalytic function permitting to produce the ether compound via reaction from at least an alcohol (I) and an alcohol (II). This catalytic function may be obtained by the use of groups directly grafted or supported to said particles. These groups may then act as catalyst in the reaction of the present invention. —SO$_3$H is particularly efficient as both catalytic and hydrophilic functions on amphiphilic particles.

Hydrophobic nature is usually provided by the presence of hydrophobic groups such as organic chains having a hydrophobic nature. Said chains are defined as organic chains having a hydrophobic character such as these chains are soluble in a hydrophobic solvent and less soluble, notably insoluble, in water. Organic chains having a hydrophobic nature may have at least 50% wt, preferentially at least 80% wt of hydrophobic groups such as alkylated groups, or alkoxylated groups.

Hydrophobic groups are preferably alkyl chains comprising 1 to 30 carbon atoms, more preferably from 1 to 8 carbon atoms or alkoxylated groups notably comprising 1 to 10 units of ethylene oxide —CH$_2$CH$_2$O— groups The exact nature of the link existing between organic chains and the surface of the solid particles can vary in a large measure and may be for example a covalent bond, or physical adsorption more often including an electrostatic bond, an ionic bond and a hydrogen bond. Covalent bonds can be obtained by grafting or co-condensation.

The grafting rate of the particle surface by hydrophobic groups may be comprised between 5 and 90% of the original amount of hydroxyl groups, preferably between 30 and 70%. This grafting rate may be evaluated by a thermal decomposition of the particles and then calculate the amount of water formed during the decomposition. It is then possible to proceed to an extrapolation of the number of hydroxyl group.

In a preferred embodiment of the invention, the bonds between the organic chains of hydrophobic nature and the surface of the particles are covalent bonds. In this case, these are usually made covalent bonds between atoms of metal particles and organic chains, usually via oxygen atoms initially present in a hydroxyl metal group of the particle surface.

Preferably, the metal atom of these groups hydroxylated metal surface is an atom of silicon, aluminum, or titanium. In this case, the particles are formed at least partially of silicon oxide, oxy-hydroxide of aluminum and/or titanium oxide, this or these oxide (s) and/or oxy-hydroxide being at least this (s) on the surface. Thus, the particles can then be formed such oxide (s), hydroxide (s) and/or oxy-hydroxide (s) of chemical nature variable, having a surface layer of silicon oxide oxy-aluminum hydroxide and/or titanium oxide, made for example by after-treatment surface.

The organic chains covalently linked are generally introduced by this embodiment of the invention by condensation of a silanol group SiOH on the particle, according to the general reaction:

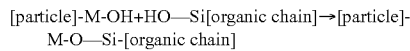
[particle]-M-OH+HO—Si[organic chain]→[particle]-M-O—Si-[organic chain]

wherein M is Si, Al or Ti.

In this case, the silanol group SiOH usually comes from the acid hydrolysis, neutral, or basic group of a alkoxysilane, for example acid hydrolysis of a compound or trimethoxyalkysilane triethoxyalkylsilane.

Whatever the exact nature of links implemented to ensure cohesion between the hydrophobic chains and the particle surface, it is preferred that the bonds between the chains and hydrophobic particles are inhomogeneously distributed on the surface of said particles, whereby said particles modified surface have a first area to overall hydrophilic nature and a second area to overall hydrophobic character.

It has to be noticed that according to the nature of hydrophilic and hydrophobic functions at the surface of particles, said particles may also act as emulsifier and also catalyst.

It is advantageous to choose the concentration of amphiphilic particles according to the invention to be greater than 0.1% by weight, particularly advantageously between 0.1% by weight and 30% by weight, based on the total weight of the preparations.

In order to obtain the alcohol (I)/alcohol (II) emulsion of step a), it is first necessary to obtain a blend of at least the alcohol (I), the alcohol (II), optionally the catalyst X and amphiphilic solid particles of nanometric dimension. The particles can be added/dispersed in either phase prior to the addition of the second phase and global emulsification. Emulsification can also be proceeded after introduction of all components in any order in the container vessel.

It is possible to produce emulsions comprising the following steps: (i) a blend of amphiphilic particles is produced in a continuous phase by addition of the particles to the liquid without stirring; and (ii) the phase to be dispersed is then added to the blend obtained in step (i) and emulsion is then obtained by stirring.

It can also be possible to produce emulsions comprising the following steps: (i) a dispersion of amphiphilic particles is produced in a continuous phase by stirring; and (ii) while stirring, the emulsion is obtained by adding the phase to be dispersed to the dispersion obtained in step (i).

Emulsification instrument can be any instrument giving high energy such as ultra sound, or high shear such as homogenizer, or other stirring methods.

The medium comprising at least alcohol (I) and alcohol (II) preferably comprise less than 10% wt of water, based on the total weight of the medium.

Preferably, the medium used in the present process of the invention is substantially free or, in some cases, completely free of any surfactant, at the start of the reaction. As used herein, the term "surfactant" refers to materials that have an amphiphilic molecular structure, which includes a polar hydrophilic molecular moiety and a nonpolar lipophilic molecular moiety, and which acts to lower the interfacial tension between the dispersed phase and the continuous phase in an emulsion. As will be appreciated, surfactants can be classified as ionic (anionic, cationic, and amphoteric) or nonionic. As used herein, the term "substantially free" when used with reference to the absence of surfactant in the medium of the present invention, means that the emulsion comprises less than 0.1% wt of surfactant, based on the total weight of the medium, notably at the beginning of the reaction; and preferably during the reaction. As used herein, the term "completely free" when used with reference to the absence of surfactant in the medium of the present invention, means that the emulsion comprises no surfactant at all.

In step b), the reaction of deshydratation is led by setting the appropriate temperature. Said temperature to lead the deshydratation reaction from alcohol (I) and alcohol (II) is of course linked to the nature of alcohol (I) and alcohol (II). The reaction temperature used in step b) to proceed with the reaction is generally comprised between 50° C. and 250° C., preferably between 130° C. and 150° C.

Several stirring methods may be used during the reaction; preferably a continuous stirring is maintained in step b). During this step, the reaction may be carried out under atmospheric pressure or under pressure. Said reaction can be made under inert gas or air for example.

Several known methods of purification of the ether compound at the end of the reaction may be used, such as for example extraction, distillation, and/or crystallisation.

Notably when reaction of the present invention permits to obtain a mono alkyl glyceryl ether, called as MAGE, as ether compound, from a mono-alcohol and a poly-alcohol, the isolation may be carried out accordingly: After finishing the reaction, ethanol is added into the reaction mixture and a part of this solution is taken out for GC analysis. The rest of the solution is filtered to remove the insoluble particles and precipitations. The filtrate is then neutralized with an ion exchange resin and concentrated by rotavap. The crude product of MAGEs could be then obtained after that unreacted mono-alcohol is completely removed under vacuum at 120° C.

Illustrating the invention are the following examples that are not to be considered as limiting the invention to their details.

EXPERIMENTAL PART

Example 1

Preparation of Amphiphilic Solid Particles of Nanometric Dimension

Materials: Aerosil 200 from Evonik Degussa, Hexamethyldisilazane (HMDSA): [(CH$_3$)$_3$Si]$_2$NH from Aldrich
Sample Pre-Treatment:
Aerosil 200 was pre-heated in oven 100° C. overnight.
Toluene (AR degree) was dried by calcined zeolite 4A.

1. Synthesis of Trimethylsilyl-Functionalized Silica

Aerosil 200 (5 g) was added into a round flask with three-neck, and then dried at 150° C. for 1 h under argon flow and then for 2 h under vacuum. Toluene (150 mL) and the required amount of HMDSA (0 uL, 152 uL, 304 uL, 457 uL, 608 uL, mol(HMDSA):mol(SiOH)=0, 0.25, 0.5, 0.75, 1) were added under argon. The solution was heated at 80° C. for 24 h. The resulting functionalized silica was then isolated by filtration and intensively washed with toluene and ethanol before being dried at 80° C. for 24 h. Finally, a series of functionalized silicas ($SiO_2$-0%, $SiO_2$-25%, $SiO_2$-50%, $SiO_2$-75% and $SiO_2$-100%) were obtained.

Example 2

Preparation of Amphiphilic and Catalytic Solid Particles of Nanometric Dimension 2.1 Synthesis of Bifunctionalized Silica with Propyl and Sulfonic Groups Materials: Aerosil 200 from Evonik Degussa, (3-mercapto-propyl)trimethoxysilane, propyltrimethoxysilane, toluene, 4-toluenesulfonic acid Sample Pre-Treatment:

Aerosil 200 was pre-heated in oven 100° C. overnight. Toluene (AR degree) was dried by calcined zeolite 4A.

(3-mercapto-propyl)trimethoxysilane: $(OMe)_3Si(CH_2)_3SH$;

propyltrimethoxysilane: $(OMe)_3Si(CH_2)_3$ 2.1.1 Grafting Propyl and Mecrapto Functions onto Silica Aerosil 200 (0.5 g) was added into a round flask, and then toluene (50 mL) was added. The mixture was stirred until homogenous distribution of aerosol 200 in the solvent. 4-toluene sulfonic acid (0.0033 g) and required amount of silanes [100%: 1.9 mL of $(OMe)_3Si(CH_2)_3SH$; 80%: 1.5 mL of $(OMe)_3Si(CH_2)_3SH$ and 0.4 mL of $(OMe)_3Si(CH_2)_3$; 50%: 0.95 mL of $(OMe)_3Si(CH_2)_3SH$ and 0.95 mL of $(OMe)_3Si(CH_2)_3$; 20%: 0.4 mL of $(OMe)_3Si(CH_2)_3SH$ and 1.5 mL of $(OMe)_3Si(CH_2)_3$] were placed into the above mixture. Then, flask was placed on a pre-heated hotplate (120° C.) and the final mixture was stirred for 4 h. After cooling down to room temperature, the resulting functionalized silica was then isolated by filtration and intensively washed with toluene and ethanol before being dried at 100° C. overnight.

2.1.2 $H_2O_2$ Oxidation

The above samples were placed in a round flask. $H_2O_2$ (30 wt %, $m(H_2O_2)$: m(sample)=60:1) was added into flask and the mixtures were stirred at 40° C. for 24 h. After filtration and washing by ethanol (95%), the solids were dried at 40° C. under vacuum for 4 h.

2.1.3 Acidification

The obtained solids and $H_2SO_4$ solution (0.8 M, $m(H_2SO_4)$: m(sample)=60:1) were added in a flask. The mixtures were stirred at room temperature for 2 h. After filtration and washing by ethanol (95%) until suspension pH equal to 7, the obtained solids were dried at 100° C.

2.2 Synthesis of Bifunctionalized Silica with Octadecyl and Sulfonic Groups

Bifunctionalized silicas with octadecyl and sulfonic groups have been synthesized according to co-condensation method. A solution of EtOH (200 ml) and $H_2O$ (28 ml) and $NH_4OH$ (16.2 ml, 25~28%) was stirred at 40° C. for 10 minutes. A second solution of tetraethyl orthosilicate (TEOS, 9.3 g) in EtOH (9.3 g) was then dropwise added in the first one during 15 minutes. After pre-hydrolysis of TEOS for 15 minutes, a mixture of $(OMe)_3Si(CH_2)_3SH$ (0.41 ml) and $(OMe)_3Si(CH_2)_{17}CH_3$ (4.10 ml, SH: C18=0.2) was dropwise introduced in the above mixture. The resulting sol-gel solution was stirred in a closed flask at 40° C. for 24 h. After centrifuging and washing with de-ionized water, the obtained solid, named as $SiO_2$-CC-20%, was freeze dried overnight. Then the procedure of oxidation and acidification of mercapto group into sulfonic group was same as described above.

2.3 Synthesis of Polystyrene(PSt)-co-Poly(styrenic sulfonic acid)(SSA) Funtionalized Silica 2.3.1 Synthesis of Random Copolymer Polystyrene(PSt)-co-Poly(styrenic sulfonic acid)(SSA)

First, PSt was synthesized through Atom transfer radical polymerization protocol: styrene, initiator (4-(bromomethyl) benzoic acid), copper chloride and 2,2'-bipyridine were feeded in a Schlenk tube in the molar ratio of 400:1:1:3. After the mixture was degassed by three freeze-vacuum-thaw cycles, the tube was put in the oil bath preset at 110° C. The conversion of St was followed by $^1H$ NMR characterization. The polymerization was stopped at expected conversion. The mixture was cooled and diluted with THF. The solution passed through a short neutral alumina column to remove the copper salts. The obtained solution was concentrated and precipitated in methanol. The polymer PSt was obtained after drying in vacuum oven at 40° C. overnight.

Secondly, the obtained PSt was sulfonated to desired extent as following: 0.92 ml acetic anhydride (9.76 mmol) and 0.26 ml sulfuric acid 98% (4.88 mmol) were added to a flask charged with 15 mL of 1,2-dichloroethane. 1.0 g PSt (9.61 mmol equivalent styrene unit) were added. The mixture turned brown and was stirred at room temperature overnight. The obtained solution was concentrated and precipitated in diethyl ether. The brown polymer was dried in vacuum oven at 40° C. overnight. The sulfonation degree could be characterized by $^1H$ NMR in acetone-d6 and titrated with NaOH standard solution, respectively.

2.3.2 Preparation of PSt-co-PSSA Grafted Silica Nanoparticles 200 mL of dried toluene was added into a 3 neck round bottomed flask charged with predried silica particles (10 g), under a nitrogen flow, ((Chloromethyl)phenylethyl) trimethoxysilane (CPMS, 16.67 ml, 67.92 mmol) was added and the mixture was refluxed for 16 h. Toluene was evaporated and the particles were purified by several dispersion and centrifugation cycles in ethanol and then acetone. The CPMS-grafted particles were dried in vacuo at 60° C. overnight. TGA showed 4.5% weight of CPMS. FTIR confirmed the presence of CPMS specific vibration bands.

A mixture of 500 mg above CPMS grafted silica (0.082 mmol ATRP sites), 20 mL of styrene (174 mmol), 9 mg $CuCl_2$ (0.0656 mmol) and 225.4 mg 2,2'-bipyridine (1.4432 mmol) were charged in a 50 mL Schlenk. After 3 freeze thaw cycles, CuCl (65 mg, 0.656 mmol) was added under a nitrogen flow. The flask was evacuated and refilled with nitrogen 3 times. The polymerization was performed at 90° C. for 29 hrs. same work-up procedure as that of linear polymer preparation was followed, and the obtained PSt grafted silica was sulfonated using the same procedure described for random PSt-co-PSSA. At the very end, the random copolymer grafted silica nanoparticles (540 mg) was obtained by lyophilization from water. Titration with NaOH solution gave the acidity of 2.05 mmol/g.

Example 3

Stability of Emulsions

The results on emulsion stability shown lower are obtained from emulsions prepared from the protocol hereafter described: The samples consist of glycerol, dodecanol and particles at different concentration. The total weight of the sample is fixed at 20 g. The weight ratio of glycerol to dodecanol is fixed to 6/4. Because the glycerol is denser and more viscous, it is first weighted and introduced in the glass bottle. The particle powder is then introduced in the desired amount prior to the dodecanol. The samples are conditioned in the oven for 48 h at 40° C. to allow the particles to be wetted. After this conditioning time, the sample is emulsified with a homogenizer ultra turrax type for 2 minutes at 13,000 rpm in a water bath at a temperature of 70° C.

The proportion of macroscopic Glycerol/Dodecanol emulsion according to time is evaluated in Table 1:

TABLE 1

| Particle concentration (% wt) | Time needed to reach 50% of separation (min) |
| --- | --- |
| 0 | 0.5 |
| 0.1 | 5 |
| 0.25 | 7.5 |
| 0.5 | 36 |
| 1 | 143 |

Right after emulsification, the volume of emulsified phase is monitored over time by image analysis of pictures taken regularly. When total separation occurs we distinguish clearly two phases, at this point we consider that there is 100% of separation. A given percentage P % of separation means that 100-P % of the total volume of the sample is made of the emulsion.

It appears then that presence of amphiphilic silica particles within the Glycerol/Dodecanol emulsion permits to stabilize the emulsion. It has to be further noticed that up to 1% wt of silica particles the higher the particles concentration the better stabilized is the emulsion.

Example 4

Stability of Emulsions and Comparisons

Several emulsifiers were used according to example 2:
SDS: Sodium dodecyl sulfate from Sinopharm Chemical Reagent Co.
AEO7: Fatty alcohol polyoxyethylene (7) ether from Rhodia, Rhodasurf L-7/90
SiO2—50% graft—0.5%
The proportion of macroscopic Glycerol/Dodecanol emulsion according to time is evaluated in Table 2:

TABLE 2

| Emulsifier (% wt) | Time needed to reach 50% of separation (min) |
| --- | --- |
| None | 0.5 |
| SiO2-50% graft-0.5% | 29 |
| SDS-1% | 3.5 |
| AEO7-1% | 1 |

Amphiphilic silica of the invention permits to improve stabilization of emulsion in comparison with other classical surfactants, even at lower weight concentration.

Example 5

MAGE Synthesis

Synthesis reaction is made by addition of glycerol and dodecanol as previously mentioned with addition of PTSA catalyst (p-toluenesolufonic acid) to obtain the emulsion and then reacting media is mechanically stirred at a temperature of 150° C. for 6 hours).

Synthesis reaction that is occurring is the following:

$$C_{12}H_{25}OH + n\,HO\text{-CH}_2\text{-CH(OH)-CH}_2\text{-OH} \xrightarrow[\text{silica particles}]{\text{catalyst}} C_{12}H_{25}\text{-}[O\text{-CH}_2\text{-CH(OH)-CH}_2]_n\text{-O-H} + n\,H_2O$$

Conversion, Yield and Selectivity results are mentioned in Table 3:

TABLE 3

| Emulsifier (% wt) | Conversion of Dodecanol (%) | Yield of MAGE1 (%) | Selectivity of MAGE1 (%) |
| --- | --- | --- | --- |
| None | 49.2 | 3.32 | 6.7 |
| Sil.(25%, 1 wt %) | 37.2 | 4.52 | 12.1 |
| Sil.(25%, 0.5 wt %) | 36.4 | 4.38 | 12 |
| Sil.(25%, 2 wt %) | 33.3 | 4.35 | 13.1 |
| PSt-co-PSSA (5% molar to Dodecanol, see 2.3.1) | 49.0 | 13.7 | 12.0 |
| PS-co-PSSA-g-Sil. (5% molar to Dodecanol, see 2.3.2) | 56.7 | 27.0 | 20.0 |

It appears that if the yield of mono-glycerol dodecyl ether (Mage1) is not significantly improved, the selectivity of Mage1 to dodecyl ether is doubled. This means that less homo-etherification happens in presence of particles than without. Comparison with small molecules modified silica particles, PS-co-PSSA based catalysts show higher yield of and better selectivity to MAGE1 due to its higher acidic capacity Example 6

Heterogeneous Catalysts for the Etherification Reactions

Reaction 1:

[Reaction scheme: 1-phenylethanol + glycerol → ether product + ...]

-continued

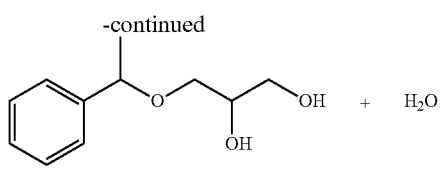

Reaction 2:

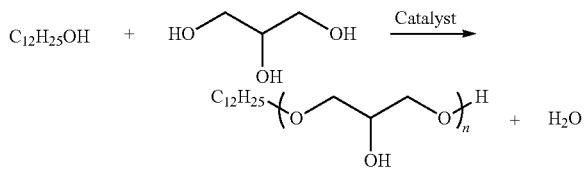

Silica materials (SiO$_2$-CC-20%) bearing long carbon chain (C18) and sulfonic group (C3-SO$_3$H) have been used to catalyze two-phase etherification reactions: one is the etherification of phenyl ethanol and glycerol in the presence of water; another is the etherification of dodecanol and glycerol as showed above. Conversions, product yield, selectivity of target product and reaction conditions were listed in Table 4.

TABLE 4

| Reaction 1 | Product yield (%) | | |
|---|---|---|---|
| PTSA | 25 | | |
| SiO$_2$-CC-20% | 56 | | |
| Reaction 2 | Conversion of dodecanol (%) | Yield of MAGE (%) | Selectivity of MAGE (%) |
| SiO$_2$-CC-20% | 18.9 | 2.3 | 12.2 |

Reaction 1 condition: Phenyl ethanol:glycerol:catalyst (H$^+$):H$_2$O = 1:4:0.017:0.17 (mol. ratio), T: 80° C., 4.5 h
Reaction 2 condition: Dodecanol:glycerol:catalyst (H$^+$) = 1:4:0.5 (mol. ratio), T: 130° C., 24 h Silica materials bearing with long alkyl chains and sulfonic groups have showed better catalytically activity than homogenous catalyst PTSA on the etherification of phenyl ethanol and glycerol in two phases. This result indicated that the better emulsion brought by silica materials probably make the increase of product yield. This type of silica materials also showed good activity on the etherification of dodecanol and glycerol due to the bifunctional efforts of emulsion and catalytic sites on materials.

What is claimed is:

1. A process to produce at least an ether compound via a reaction from at least an alcohol (I) and an alcohol (II), optionally using a catalyst X, wherein alcohol (I) and alcohol (II) form a biphasic liquid system when mixed together; the process comprising at least the following steps:
  a) Producing an alcohol (I)/alcohol (II) emulsion by using as stabilizing species amphiphilic solid particles of nanometric dimension; optionally comprising a catalyst X;
  b) Proceeding to the reaction of the ether compound by setting temperature, and
  c) Isolating the ether compound.

2. The process according to claim 1, wherein the medium used in the process is substantially free of any surfactant, at the start of the reaction.

3. The process according to claim 1, wherein the emulsion comprises less than 0.1% wt of surfactant, based on the total weight of the medium.

4. The process according to claim 1, wherein the medium comprises less than 10% wt of water, based on the total weight of the medium.

5. The process according to claim 1, wherein the immiscibility of alcohol (I) and alcohol (II) is defined according to the following protocol P: 50% vol of alcohol (I) and 50% vol of alcohol (II) are blended together and set a temperature T of 5° C. above the highest melting point of alcohol (I) or alcohol (II), and under atmospheric pressure; then the blend is stirred for 5 mins and 30 mins settling.

6. The process according to claim 1, wherein alcohol (I) is a hydrophilic alcohol (I) of formula (I) as follows:

$$R^1(OH)p \quad (I)$$

wherein R$^1$ represents the skeleton moiety of the alcohol, p is an integer ranging from 1 to 20.

7. The process according to claim 6, wherein R$^1$ represents the skeleton moiety of a glycerol with p is 3.

8. The process according to claim 1, wherein alcohol (I) is chosen in the group consisting of: ethylene glycol, diethylene glycol, polyethylene glycol, propylene glycol, dipropylene glycol, polypropylene glycol, 1,4-butylene glycol, 1,6-hexylene glycol, 1,8-octylene glycol, 1,10-decylene glycol, neopentyl glycol, trimethylol ethane, trimethylol propane, glycerol, diglycerol, pentaerythritol and sorbitol.

9. The process according to claim 1, wherein alcohol (II) is a hydrophobic alcohol (II) of formula (II) as follows:

$$R^2(OH) \quad (II)$$

wherein R$^2$ represents an alkyl, aryl, alkenyl or alkoxy radical comprising 6 to 36 carbon atoms, R$^2$ optionally comprises one or several heteroatom(s).

10. The process according to claim 1, wherein alcohol (II) is chosen in the group consisting of: 2-ethylhexyl alcohol, octyl alcohol, decyl alcohol, lauryl alcohol (dodecanol), myristyl alcohol, palmityl alcohol, stearyl alcohol, isostearyl alcohol, oleyl alcohol, ethylene glycol monomethyl ether, ethylene glycol monoethyl ether, ethylene glycol monopropyl ether, ethylene glycol monobutyl ether, propylene glycol monomethyl ether, propylene glycol monoethyl ether, propylene glycol monopropyl ether, propylene glycol monobutyl ether, polyethylene glycol monomethyl ether, polyethylene glycol monoethyl ether, polyethylene glycol monopropyl ether, polyethylene glycol monobutyl ether, polypropylene glycol monomethyl ether, polypropylene glycol monoethyl ether, polypropylene glycol monopropyl ether and polypropylene glycol monobutyl ether.

11. The process according to claim 1, wherein the molar ratio of alcohol (I) to alcohol (II) is from 0.01 to 50.

12. The process according to claim 1, wherein the ether compound is a mono alkyl glyceryl ether of formula (III) as follows:

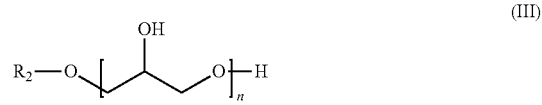

wherein R$^2$ represents an alkyl, aryl, alkenyl or alkoxy radical comprising 6 to 36 carbon atoms, R$^2$ optionally comprises one or several heteroatom(s); and n is comprised between 1 and 20.

13. The process according to claim 1, wherein the catalyst is a sulfonic acid catalyst.

14. The process according to claim 1, wherein the concentration of amphiphilic particles is comprised between 0.1% and 30% by weight, based on the total weight of the preparation.

15. The process according to claim 1, wherein the reaction temperature used in step b) to proceed with the reaction is comprised between 50° C. and 250° C.

16. The process according to claim 1, wherein the ether compound in step c) is isolated by extraction, distillation, and/or crystallisation.

17. The process according to claim 1, wherein amphiphilic solid particles of nanometric dimension provide a catalytic function permitting to produce the ether compound via reaction from at least an alcohol (I) and an alcohol (II).

18. The process according to claim 17, wherein amphiphilic solid particles of nanometric dimension provide —$SO_3H$ groups directly grafted or supported to said particles.

19. The process according to claim 11, wherein the molar ratio of alcohol (I) to alcohol (II) is from 0.5 to 4.

20. The process according to claim 15, wherein the reaction temperature used in step b) to proceed with the reaction is comprised between 130° C. and 150° C.

* * * * *